(12) United States Patent
Meriheinä et al.

(10) Patent No.: US 10,178,964 B2
(45) Date of Patent: Jan. 15, 2019

(54) HEART MONITORING SYSTEM

(71) Applicants: MURATA MANUFACTURING CO., LTD., Nagaokakyo-shi, Kyoto (JP); PRECORDIOR OY, Turku (FI)

(72) Inventors: Ulf Meriheinä, Söderkulla (FI); Marika Juppo, Espoo (FI); Tero Koivisto, Turku (FI); Mikko Pänäälä, Raisio (FI); Kati Sairanen, Naantali (FI); Markus Grönholm, Turku (FI)

(73) Assignees: Murata Manufacturing Co., Ltd., Nagaokakyo-shi, Kyoto (JP); Precordior Oy, Turku (FI)

( * ) Notice: Subject to any disclaimer, the term of this patent is extended or adjusted under 35 U.S.C. 154(b) by 0 days.

(21) Appl. No.: 14/917,350

(22) PCT Filed: Sep. 10, 2014

(86) PCT No.: PCT/IB2014/064377
§ 371 (c)(1),
(2) Date: Mar. 8, 2016

(87) PCT Pub. No.: WO2015/036925
PCT Pub. Date: Mar. 19, 2015

(65) Prior Publication Data
US 2016/0220152 A1    Aug. 4, 2016

(30) Foreign Application Priority Data
Sep. 13, 2013 (FI) ............................ 20135924

(51) Int. Cl.
*A61B 5/11* (2006.01)
*A61B 5/00* (2006.01)
(Continued)

(52) U.S. Cl.
CPC ............ *A61B 5/1102* (2013.01); *A61B 5/113* (2013.01); *A61B 5/1107* (2013.01);
(Continued)

(58) Field of Classification Search
None
See application file for complete search history.

(56) References Cited

U.S. PATENT DOCUMENTS 6,662,032 B1 * 12/2003 Gavish ................. A61B 5/0205
600/300
8,475,367 B1 * 7/2013 Yuen .................... G06F 19/3418
128/920
(Continued)

FOREIGN PATENT DOCUMENTS

| CN | 102458237 A | 5/2012 |
| EP | 2 198 916 A1 | 6/2010 |

(Continued)

OTHER PUBLICATIONS

Ryan K. Albright et al., "OLAM: A Wearable, Non-Contact Sensor for continuous Heart-Rate and Activity Monitoring", 33rd Annual International Conference of the IEEE EMBS; Aug. 30-Sep. 3, 2011; pp. 5625-5628.
(Continued)

*Primary Examiner* — Erica S Lee
(74) *Attorney, Agent, or Firm* — Squire Patton Boggs (US) LLP

(57) ABSTRACT

A device that includes a sensor of angular motion configured to obtain an angular ballistograph signal indicative of rotational movement of a chest of a subject. Signal processing means are configured to generate from this angular ballistocardiograph signal measured values of an output parameter, which is indicative of cardiac operation of the subject.

52 Claims, 9 Drawing Sheets

(51) Int. Cl.
*G01C 19/5783* (2012.01)
*A61B 5/113* (2006.01)
*A61B 5/046* (2006.01)

(52) U.S. Cl.
CPC .......... *A61B 5/1121* (2013.01); *A61B 5/6823* (2013.01); *A61B 5/7246* (2013.01); *A61B 5/7278* (2013.01); *A61B 5/7282* (2013.01); *A61B 5/746* (2013.01); *G01C 19/5783* (2013.01); *A61B 5/046* (2013.01); *A61B 2562/028* (2013.01); *A61B 2562/0219* (2013.01)

(56) References Cited

U.S. PATENT DOCUMENTS

| | | | |
|---|---|---|---|
| 8,870,780 B2* | 10/2014 | Inan | A61B 5/029 600/481 |
| 2007/0032749 A1* | 2/2007 | Overall | A61B 5/02444 600/595 |
| 2010/0016685 A1* | 1/2010 | Muehlsteff | A61B 5/02444 600/301 |
| 2013/0041269 A1 | 2/2013 | Stahmann et al. | |
| 2013/0109989 A1* | 5/2013 | Busse | A61B 5/1102 600/527 |
| 2015/0133806 A1* | 5/2015 | Airaksinen | A61B 5/7246 600/513 |

FOREIGN PATENT DOCUMENTS

| | | |
|---|---|---|
| JP | 2012-105762 A | 6/2012 |
| WO | 2010/145009 A1 | 12/2010 |
| WO | WO 2010/145009 A1 | 12/2010 |
| WO | 2012/092303 A1 | 7/2012 |
| WO | 2013/121431 A1 | 8/2013 |
| WO | WO 2013/121431 A1 | 8/2013 |

OTHER PUBLICATIONS

D.E. Beisher et al., "Ballistocardiograph Research Society", The American Journal of Cardiology, May 1961; p. 302.
Paolo Castiglioni et al., "Wearable Seismocardiography", IEEE, 2007; pp. 3954-3957.
S. De Ridder et al., "Three-Dimensional Ballistocardiography in Microgravity: A Review of Past Research", 33rd Annual International Conference of the IEEE EMBS; Aug. 30-Sep. 3, 2011, pp. 4267-4270.
Finnish Search Report application No. 20135924 dated Jun. 2, 2014.
International Search Report & Written Opinion dated Nov. 21, 2014 corresponding to International Patent Application No. PCT/IB2014/064377.
International Preliminary Report on Patentability dated Jan. 21, 2016 corresponding to International Patent Application No. PCT/IB2014/064377.
Patent Office of the People's Republic of China, Search Report corresponding to Appln. No. 201480050421.3, Nov. 27, 2017.

* cited by examiner

HEART MONITORING SYSTEM

FIELD OF THE INVENTION

The present invention relates to monitoring vital signs of a user and especially to a system, method and a computer program product for monitoring cardiac operation of a subject, defined in preambles of the independent claims.

BACKGROUND OF THE INVENTION

A heart is a hollow tissue formed of cells that are capable of producing a contraction that changes the length and shape of the cell. Heart pumps blood in cyclic contractions through a network of arteries and veins called the cardiovascular system. As shown in FIG. 1, a human heart includes four chambers, which are divided by a septum into a right side (right atrium RA and right ventricle RV) and a left side (left atrium LA and left ventricle LV). During a heartbeat cycle, the right atrium RA receives blood from the veins and pumps it into the right ventricle and the right ventricle RV pumps the blood into the lungs for oxygenation. The left atrium LA receives the oxygenated blood from the lungs and pumps it to the left ventricle LV, and the left ventricle LV pumps the blood into the veins. The apex AP of the heart is a portion formed by the inferolateral part of the left ventricle LV.

Various techniques have been developed to provide measurable parameters that are indicative of cardiac operation of a monitored subject. Many of these techniques are invasive and therefore suitable for advanced medical use only.

In the noninvasive side, echocardiography is a technique that applies ultrasound to provide an image of the heart. Echocardiography can be comfortably carried out at the bedside, and it has therefore become a widely-used tool for noninvasive studies on cardiac mechanics of diseased and healthy hearts. The produced images require, however, complex and basically immobile computer equipment and the images need to be interpreted by a highly trained physician. Ambulatory or long-term monitoring of the cardiac operation outside the clinical environment by echocardiography is practically impossible.

Electrocardiography is based on measuring electrical activity of the heart with electrodes attached to the surface of the skin of the monitored subject. In electrocardiography, wave depolarization of the heart is detected as changes of voltage between a pair of electrodes placed in specific positions on the skin. Typically a number of electrodes are used, and they are arranged in combination into pairs (leads). Electrocardiograms are very accurate and widely used, and also allow some computerized interpretation. Proper placement of the electrodes may, however, be challenging for users without medical training. In addition, the measurement system typically requires a computerized system connected with cables to a plurality of self-adhesive pads that couple through conducting gel to the skin of the monitored subject. Moving with such wiring is very limited.

Patent publication WO2010145009 discloses an apparatus for determining information indicative of physiological condition of a subject. The apparatus comprises a sensor device that obtains ballistocardiograph data indicative of heart motion of the subject, measured along a plurality of spatial axes. Ballistocardiograph data indicates the extent of mechanical movements of a body that take place in response to the myocardial activity of the heart. This ballistocardiograph data is then used to process data that is indicative of heart motion of the subject. This prior art method overcomes some of the limitations of the prior art. However, it has been noted that the linear measurement along spatial axes is strongly affected by the posture of the monitored subject during the measurement. In addition, some characteristics of the heartbeat cycle are not completely reliably measurable with the linear motion data.

BRIEF DESCRIPTION OF THE INVENTION

The object of the present invention is to provide a non-invasive cardiac operation monitoring solution where at least one of disadvantages of the prior art is eliminated or at least alleviated. The objects of the present invention are achieved with a system, method and computer program product according to the characterizing portions of the independent claims.

The preferred embodiments of the invention are disclosed in the dependent claims.

Due to a specific orientation of the myocardial fibers, in a heartbeat cycle the heart makes rotation along its long-axis and a wringing (twisting) motion. Torsional squeezing and opening of the left ventricle LV caused by heart rotation stands for about 60% of the stroke volume of the heart. The rest may be considered to result from the deflection of a wall between the left ventricle LV and the left atrium LA, and from the linear squeezing of the left ventricle LV from the apex AP.

The present invention discloses a device that includes a sensor of angular motion configured to obtain an angular ballistograph signal indicative of rotational movement of a chest of a subject. Signal processing means are configured to generate from this angular ballistocardiograph signal measured values of an output parameter, which is indicative of cardiac operation of the subject. The generated values or parameters can be used in a stand-alone system or in combination to improve signals and/or analysis made in a system that applies one or more of the prior art techniques.

The signal of a sensor of angular motion is not affected by gravity, which makes the measurement practically independent of the position or posture of the monitored subject. It has been noted that the external angular motion of the chest is orders of magnitude larger than what one would anticipate from the mere extent of the heart rotation and the ratio between the size of the heart and the diameter of the human chest. It has also been noted that the detection of the angular motion is also relatively insensitive to the location of the sensor in respect to the heart. Due to these aspects, accurate measurements can be made with even one gyroscope, for example microelectromechanical gyroscope, attached to the chest of the monitored subject. Microelectromechanical gyroscopes are accurate, small in size and commercially well available.

These and further advantages of the invention are discussed in more detail in the following with detailed descriptions of some embodiments of the invention.

BRIEF DESCRIPTION OF THE FIGURES

In the following the invention will be described in greater detail, in connection with preferred embodiments, with reference to the attached drawings, in which.

DETAILED DESCRIPTION OF SOME EMBODIMENTS

The following embodiments are exemplary. Although the specification may refer to "an", "one", or "some" embodiment(s), this does not necessarily mean that each such reference is to the same embodiment(s), or that the feature only applies to a single embodiment. Single features of different embodiments may be combined to provide further embodiments.

In the following, features of the invention will be described with a simple example of a device architecture in which various embodiments of the invention may be implemented. Only elements relevant for illustrating the embodiments are described in detail. Various implementations of heart monitoring systems and methods comprise elements that are generally known to a person skilled in the art and may not be specifically described herein.

The monitoring system according to the invention generates one or more output values for one or more parameters that are indicative of operation of the heart of a subject. These values may be used as such or be further processed to indicate condition of the heart of the subject. The monitoring system is herein disclosed as applied to a human subject. The invention is, however, applicable to animal species or any type of subject that has a heart and a body that responsively encloses the heart such that the heartbeat results in recoil motion of the body.

Figure 1:
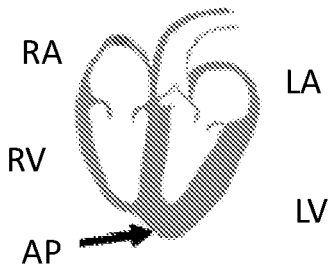
FIG. 1 illustrates elements of a human heart.
Figure 2:
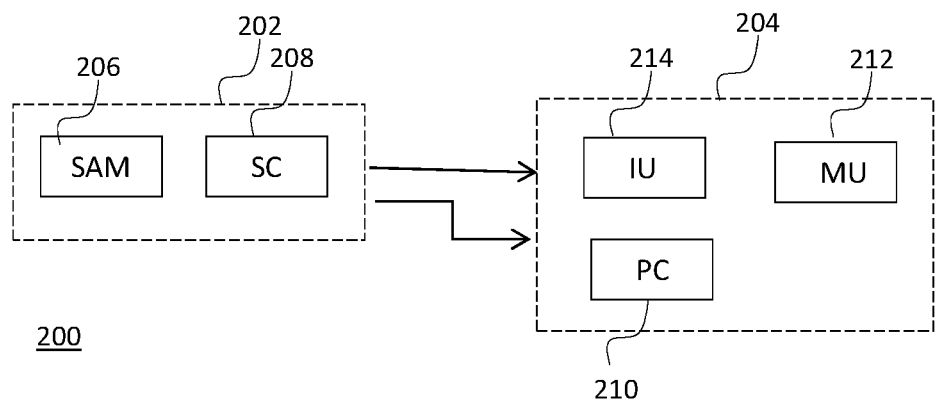
FIG. 2 illustrates functional elements of an embodiment of a monitoring system.

The block chart of FIG. 2 illustrates functional elements of an embodiment of a monitoring system 200 according to the present invention. The system includes a sensor of angular motion configured to obtain an angular ballistograph signal that is indicative of rotational movement of a chest of a subject, and signal processing means configured to generate from the angular ballistocardiograph signal measured values of an output parameter that is indicative of cardiac operation of the subject. These elements may be implemented as one physical device, for example, a mobile computing device, like a smartphone, or a tablet. Alternatively, the elements may be included in two or more electrically or communicatively coupled physical devices of the system. FIG. 2 illustrates an exemplary configuration where the system 200 comprises a sensor unit 202 and a control unit 204. In this example, the sensor unit 202 may be considered as an element to be attached to the monitored subject and the control unit 204 may be considered as an element physically detached from the monitored subject.

The sensor unit 202 includes a sensor of angular motion 206. The sensor of angular motion is configured to be attached to the subject to move along motions of the subject, or part of the subject it is attached to. Rotational movement or angular motion refers herein to circular movement in which an object progresses in radial orientation to a rotation axis. The sensor of angular motion refers here to a functional element that may be exposed to angular motion of the subject and translate at least one variable of the angular motion into an electrical signal. Applicable variables include, for example, position in radial orientation, angular velocity and angular acceleration. Rotary motion of the heart and the reverse rotary motion of the surrounding part of the body of the subject are oscillatory, so the sensor of angular motion may be configured to detect both direction and magnitude of an applied variable.

The sensor unit 202 may also include a signal conditioning unit 208 that manipulates the raw input electrical signal to meet requirements of a next stage for further processing. Signal conditioning may include, for example, isolating, filtering, amplifying, and converting a sensor input signal to a proportional output signal that may be forwarded to another control device or control system. A signal conditioning unit 208 may also perform some computation functions such as totalization, integration, pulse-width modulation, linearization, and other mathematical operations on a signal. The signal conditioning unit 208 may alternatively be included in the control unit 204.

The sensor of angular motion is configured to generate a chest motion signal, an angular ballistocardiograph signal that is indicative of rotational recoil movement on the chest in response to cardiac operation of the subject within the chest. Ballistocardiography refers in general to a technology for measuring movements of a body, which are caused in response to shifts in the center of the mass of the body during heartbeat cycles. The chest refers here to a pectoral part of the body in the upper torso between the neck and the abdomen of the subject. Advantageously, rotational movement of the chest about an axis parallel to the sagittal plane of the subject is measured. However, other axes may be applied within the scope, as well.

The sensor of angular motion 206 may be attached in a desired position and orientation to the exterior of the chest of the subject with a fastening element such that when the underlying part of the chest moves, the sensor moves accordingly. The fastening element refers here to mechanical means that may be applied to position the sensor of angular motion 206 into contact with the outer surface of the skin of the user. The fastening element may be implemented, for example, with an elastic or adjustable strap. The sensor of angular motion 206 and any electrical wiring required by its electrical connections may be attached or integrated to the strap. Other fastening mechanisms may be applied, as well. For example the fastening element may comprise one or more easily removable adhesive bands to attach the sensor of angular motion 206 on the skin in the chest area. Rotational movement of the chest of the subject may alternatively be detected with a sensor of angular motion coupled to a position in any other part of the upper torso of the subject. For example, a position in the backside of the upper torso of the subject may be applied for the purpose. Such sensor configuration allows measurements without specific fastening elements. For example, the sensor unit may be incorporated into an underlay, like a mattress on which the monitored subject may lie without additional straps and tapes.

A sensor of angular motion typically has a sense direction, which means that it is configured to sense angular motion about a specific axis of rotation. This axis of rotation defines the sense direction of the sensor of angular motion.

It is known that microelectromechanical (MEMS) structures can be applied to quickly and accurately detect very small changes in physical properties. A microelectromechanical gyroscope can be applied to quickly and accurately detect very small angular displacements. Motion has six degrees of freedom: translations in three orthogonal directions and rotations around three orthogonal axes. The latter three may be measured by an angular rate sensor, also known as a gyroscope. MEMS gyroscopes use the Coriolis Effect to measure the angular rate. When a mass is moving in one direction and rotational angular velocity is applied, the mass experiences a force in orthogonal direction as a result of the Coriolis force. The resulting physical displacement caused by the Coriolis force may then be read from, for example, a capacitively, piezoelectrically or piezoresistively sensing structure.

In MEMS gyroscopes the primary motion is typically not continuous rotation as in conventional ones due to lack of adequate bearings. Instead, mechanical oscillation may be used as the primary motion. When an oscillating gyroscope is subjected to an angular motion orthogonal to the direction of the primary motion, an undulating Coriolis force results. This creates a secondary oscillation orthogonal to the primary motion and to the axis of the angular motion, and at the frequency of the primary oscillation. The amplitude of this coupled oscillation can be used as the measure of the angular motion.

Being based on Coriolis force, the detected signal of a gyroscope is minimally affected by gravity. This makes gyrocardiograms far more insensitive to posture of the monitored subject than, for example, seismocardiograms. The subject may then freely select a comfortable position for taking a cardiogram measurement, or to some extent even move during the measurement.

During measurement the position of the sensor should optimally be as close to the heart as possible and the orientation of the sensor should be such that the sense direction is aligned as accurately to the axis of rotation of the body of the subject as possible. In a human subject, axes parallel to the sagittal plane that passes from ventral to dorsal, and divides the body into halves may be applied. These requirements for sensor positioning are easy to understand and implement. The tolerances in positioning are, in addition, reasonable, which enables fastening of the sensor unit in, for example, ambulatory environment or by people with less or no medical training.

Cardiac function typically includes various ventricular directional motions of narrowing shortening, lengthening, widening and twisting. Despite this directionality, it has been detected that the recoil effect is relatively insensitive to the position and orientation of the sensor unit. One reason for relative insensitivity to deviations in the orientation is that in theory the error is proportional to cosine of an angle between the sense direction of the sensor and a rotation axis of the rotary oscillation of the heart. It is known that in the neighborhood of zero, cosine is a slowly decreasing function. One reason for relative insensitivity to position of the sensor is that different parts of the heart couple differently to the surrounding, mostly liquid tissue. In addition, a volume of blood flowing into the aorta contributes to the detected recoil motion of the chest. The inertial volumes beyond the extent of the heart muscle itself balance the recoil effect such that reasonable deviations in the position and orientation of the sensor unit can be tolerated. In addition, the detected motion is larger and thereby provides relatively easily detectable large signals.

The control unit 204 is communicatively coupled to the sensor unit to input signals generated by the sensor of angular motion for further processing. Typically the coupling is electrical, allowing both power supply to the sensor unit, as well as wireline exchange of signals between the sensor unit and the control unit. The sensor unit may, however, be a standalone unit with own power supply and radio interface to the control unit. On the other hand, the sensor unit and control unit may be implemented as one integrated physical device.

The control unit 204 is a device that may comprise a processing component 210. The processing component 210 is a combination of one or more computing devices for performing systematic execution of operations upon predefined data. The processing component may comprise one or more arithmetic logic units, a number of special registers and control circuits. The processing component may comprise or may be connected to a memory unit 212 that provides a data medium where computer-readable data or programs, or user data can be stored. The memory unit may comprise one or more units of volatile or non-volatile memory, for example EEPROM, ROM, PROM, RAM, DRAM, SRAM, firmware, programmable logic, etc.

The control unit 204 may also comprise, or be connected to an interface unit 214 that comprises at least one input unit for inputting data to the internal processes of the control unit, and at least one output unit for outputting data from the internal processes of the control unit.

If a line interface is applied, the interface unit 214 typically comprises plug-in units acting as a gateway for information delivered to its external connection points and for information fed to the lines connected to its external connection points. If a radio interface is applied, the interface unit 214 typically comprises a radio transceiver unit, which includes a transmitter and a receiver. A transmitter of the radio transceiver unit may receive a bitstream from the processing component 210, and convert it to a radio signal for transmission by an antenna. Correspondingly, the radio signals received by the antenna may be led to a receiver of the radio transceiver unit, which converts the radio signal into a bitstream that is forwarded for further processing to the processing component 210. Different line or radio interfaces may be implemented in one interface unit.

The interface unit 214 may also comprise a user interface with a keypad, a touch screen, a microphone, or equals for inputting data and a screen, a touch screen, a loudspeaker, or equals for outputting data to a user of the device.

The processing component 210 and the interface unit 214 are electrically interconnected to provide means for performing systematic execution of operations on the received and/or stored data according to predefined, essentially programmed processes. These operations comprise the procedures described herein for the control unit of the monitoring system of FIG. 2.

Figure 3:
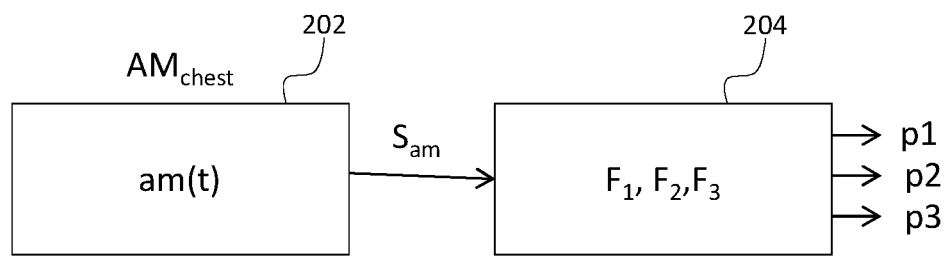
FIG. 3 illustrates functional configuration of a cardiac monitoring system.

FIG. 3 illustrates functional configuration of a cardiac monitoring system 200 that includes the sensor unit 202 and the control unit 204 of FIG. 2. The sensor unit, attached to the chest of the monitored subject is exposed to temporary angular motion $AM_{chest}$ of the chest, and undergoes a corresponding motion am(t). In response to the angular motion am(t), the sensor unit generates an angular ballistocardiograph signal $S_{am}$ and forwards it to the control unit. The control unit includes one or more data processing functions $F_1$, $F_2$, $F_3$, each of which defines a rule or correspondence between values of the angular ballistocardiograph signal $S_{am}$ and values of output parameters p1, p2, p3 that are indicative of operational parameters of the heart of the subject. The control unit may store one or more of these output parameters p1, p2, p3 to a local data storage for later processing, output one or more of them in one or more media forms through the user interface of the control unit, or transmit one or more of them to a remote node for further processing.

Figure 4:
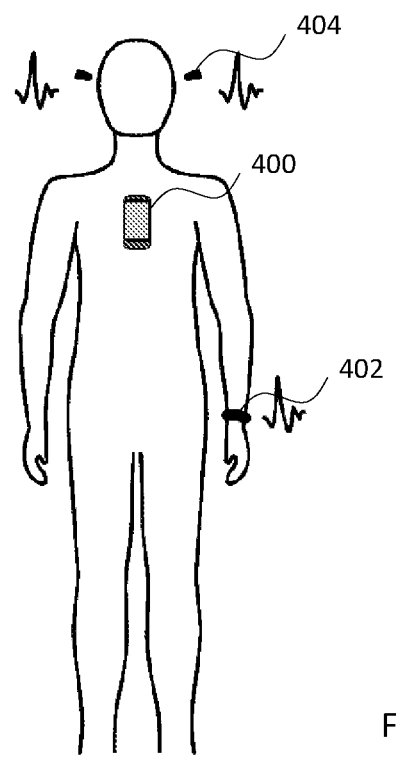
FIG. 4 illustrates another exemplary configuration of a cardiac monitoring system.

FIG. 4 illustrates another exemplary configuration where the system 400 is a mobile computing device, a smartphone that incorporates both the sensor unit and the control unit. Many of the advanced mobile computing devices today include a gyroscope apparatus, often a multi-axial gyroscope able to sense angular motion in various directions. The signal or signals from the internal gyroscope apparatus may be available, for example through an application programming interface (API) of the operating system. An application may be configured to use the gyroscope signals and the computing means of the mobile computing device, and thereby form the claimed system. The advantage of using a mobile computing device system is that the monitoring can be made with a non-dedicated device, typically available to the user in any case. The user can easily use, for example, a smartphone to take his/her own gyrocardiogram to, for example, measure heart rates, detect atrial fibrillation etc. Furthermore, processing, memory and interface means of the mobile computing device allow measured data to be stored, preprocessed or processed locally in the mobile computing device, and/or to be transmitted to a remote location for further processing, or to be analyzed, for example by a physician.

As will be discussed in more detail later on, in monitoring systems the gyroscope signal may be used in combination with other signal types. The mobile computing device of FIG. 4 may be equipped with, for example, an ECG monitoring capability by integrating ECG electrodes into a casing the mobile computing device. Such configuration enables one to combine ECG and gyroscope signals to determine, for example, cardiac time intervals.

As illustrated in FIG. 4, the mobile computing device 400 may also be connected with other apparatuses, such as a wrist-type heart rate monitor 402 (smartwatch or similar) or a set of one or two headphones 404 capable of measuring heart rates. The use of signals from two measurement points makes it possible to determine a pulse (arterial pressure pulse) transit time from the heart to some specific position, in these exemplary cases to the wrist or to the ear. When the distance between these two measurement positions is known, the pulse transit time can be used to measure various physiological parameters, such as blood pressure and arterial resistance.

Figure 5:
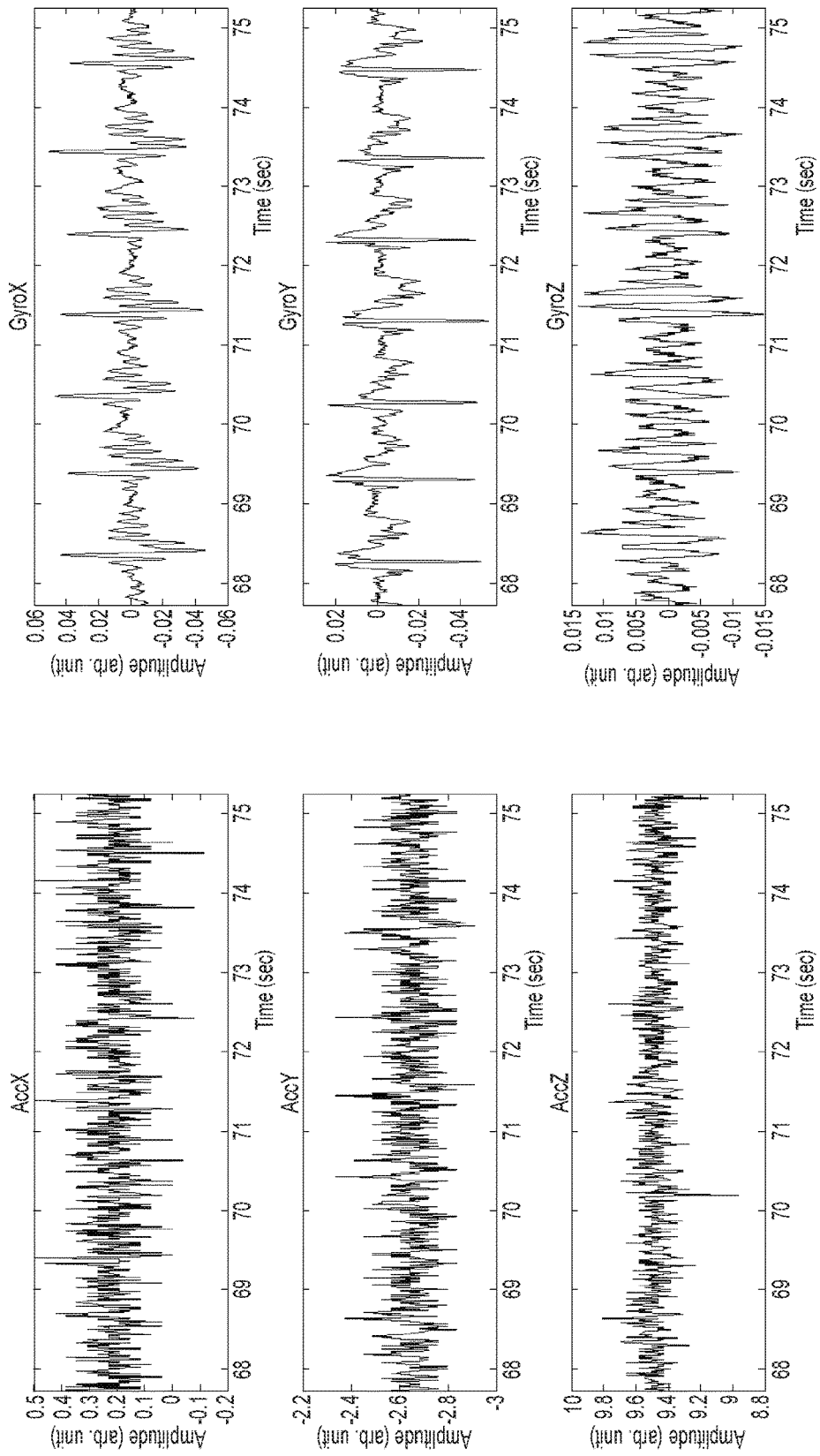
FIG. 5 illustrates measurement results taken with the system of FIG. 4.

FIG. 5 illustrates measurement results taken with the system of FIG. 4, i.e. with a smartphone attached to the chest of the user. The smartphone includes also a multi-axial accelerometer, and curves AccX, AccY, AccZ represent X-Y- and Z-direction signals from the linear accelerometer. Curves GyroX, GyroY, GyroZ represent angular motion signals about X-, Y-, and Z-direction aces from a gyroscope apparatus within the same smartphone. It may be seen that the output signal of the multi-axial gyroscope is more clear-cut and thus suitable for accurate analysis than the fuzzy output signal of the multi-axial accelerometer.

Figure 6:
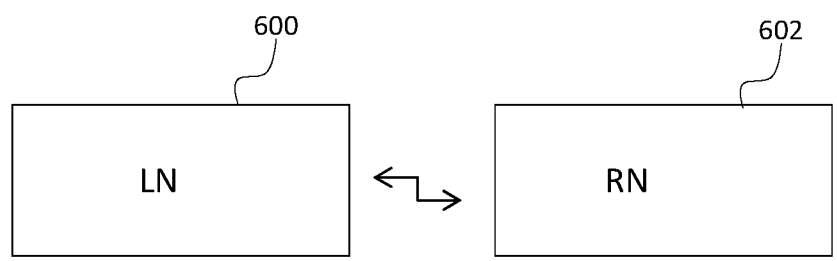
FIG. 6 illustrates a remote monitoring system including the cardiac monitoring system.

FIG. 6 illustrates a remote monitoring system including the cardiac monitoring system of FIG. 2. The system may include a local node 600 that comprises the sensor unit 202 and the control unit 204 of FIG. 2. In addition, the local node 600 may be communicatively connected to a remote node 602. The remote node 602 may be, for example, an application server that provides a monitoring application as a service to one or more users. One of the aspects monitored with the application may be the state of the heart of the user. Alternatively, the remote node may be a personal computing device into which a heart monitoring application has been installed. The local node may be a dedicated device or combination of devices including the sensor unit and the control unit described above. Alternatively, the local node may be implemented as a sensor unit that interfaces a client application in a multipurpose computer device (for example a mobile phone, a portable computing device, or network terminal of a user). A client application in the computer device may interface the sensor unit and a server application. The server application may be available in a physical remote node 602, or in a cloud of remote nodes accessible through a communication network.

While various aspects of the invention may be illustrated and described as block diagrams, message flow diagrams, flow charts and logic flow diagrams, or using some other pictorial representation, it is well understood that the illustrated units, blocks, apparatus, system elements, procedures and methods may be implemented in, for example, hardware, software, firmware, special purpose circuits or logic, a computing device or some combination thereof. Software routines, which may also be called as program products, are articles of manufacture and can be stored in any apparatus-readable data storage medium, and they include program instructions to perform particular predefined tasks. Accordingly, embodiments of this invention also provide a computer program product, readable by a computer and encoding instructions for monitoring cardiac operations of a subject in a device or a system of FIG. 2, 3, 4 or 5.

The sensor of angular motion is advantageously a microelectromechanical device, but other angular motion detection technologies may be applied, as well. For example, a magnetometer attached to the chest of the subject may be used to determine the change of position of the chest in relation to the earth's magnetic field.

Noise and other unwanted features may be removed from the raw angular ballistocardiograph signal $S_{am}$ with analog or digital filters. A low pass, high pass or band pass filter may be applied. For example, after converting the analog signal to digital form, a digital low pass filter of the form $$y(t)=(1-k)*y(t-1)+k*x(t) \quad (1)$$

where
y(t)=value of the filtered signal at time step t,
y(t−1)=value of the filtered signal at time step (t−1),
x=value of the unfiltered signal at time step t,
k=filter coefficient,
may be applied for the purpose. The filtering may also or alternatively apply polynomial fitting, for example convolution with a Savitzky-Golay filter.

Figure 7:
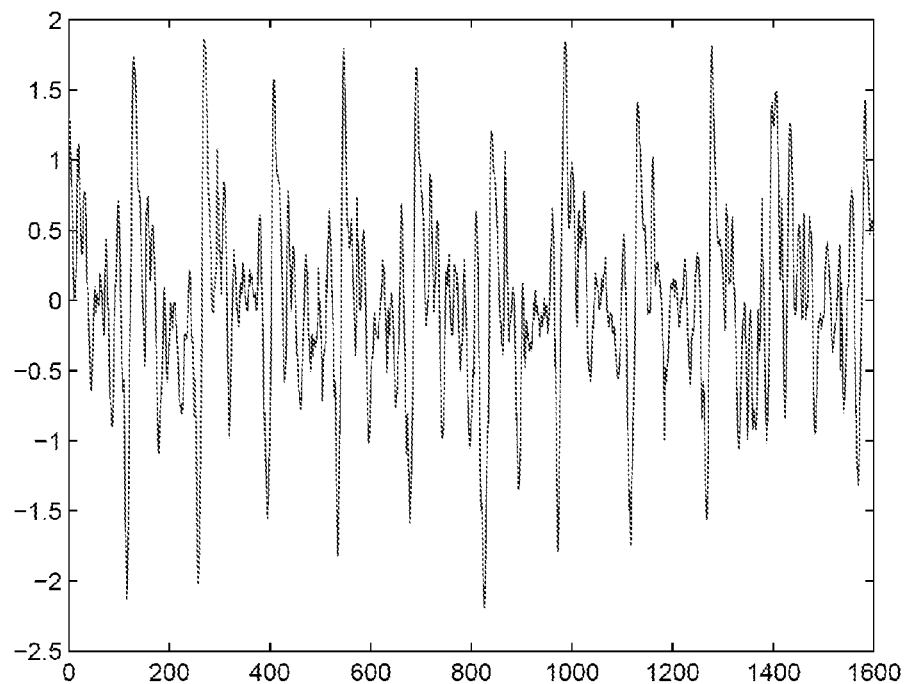
FIG. 7 illustrates an exemplary angular ballistocardiograph signal during heartbeat cycles.

The curve of FIG. 7 illustrates an exemplary filtered angular ballistocardiograph signal $S_{am}$ during heartbeat cycles of a test subject. The vertical axis represents the magnitude of sensed angular rate in the specific sense direction, and the horizontal axis represents accumulated number of time steps or elapsed time. Signal to noise ratio may be enhanced by means of matched filtering, where the filtered signal is correlated to a predefined template. The heart motion may be approximated to constitute a reciprocating motion where the heart twists in a first direction (here: positive twist), and in an opposite second direction (here: negative twist). The template may comprise a set of one or more limits for characteristics of the signal, for example specific amplitude, time domain feature or frequency domain feature.

Figure 8:
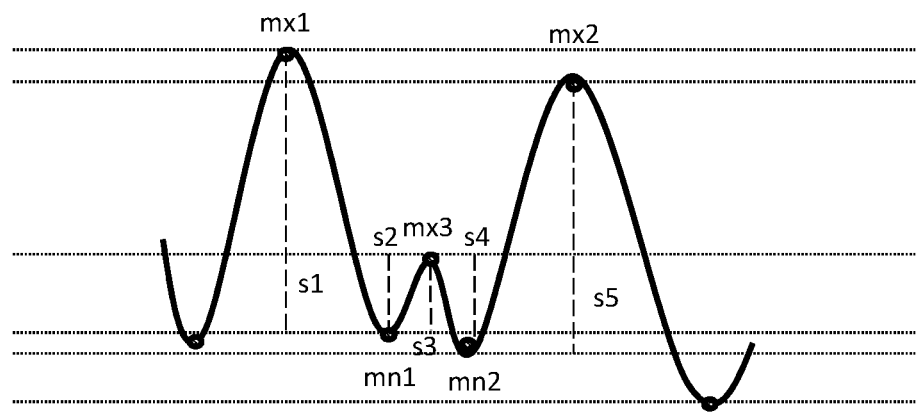
FIG. 8 shows a simplified example of an angular ballistocardiograph signal.

As a simple example, matched filtering of the angular ballistocardiograph signal $S_{am}$ of FIG. 7 may be done by means of signal extreme (minimum/maximum) values. FIG. 8 shows a simplified example of an angular ballistocardiograph signal $S_{am}$. For example, the control unit may be configured to determine consecutive maximum and minimum values mx1, mn1, mx2, mn2, mx3, mn3, . . . and determine slopes s1, s2, . . . between them, as shown in FIG. 6.

$$s1=mx1-mn1$$

$$s2=mx2-mn1$$

$$s3=mx2-mn2$$

$$s4=mx3-mn2$$

etc.

Figure 9:
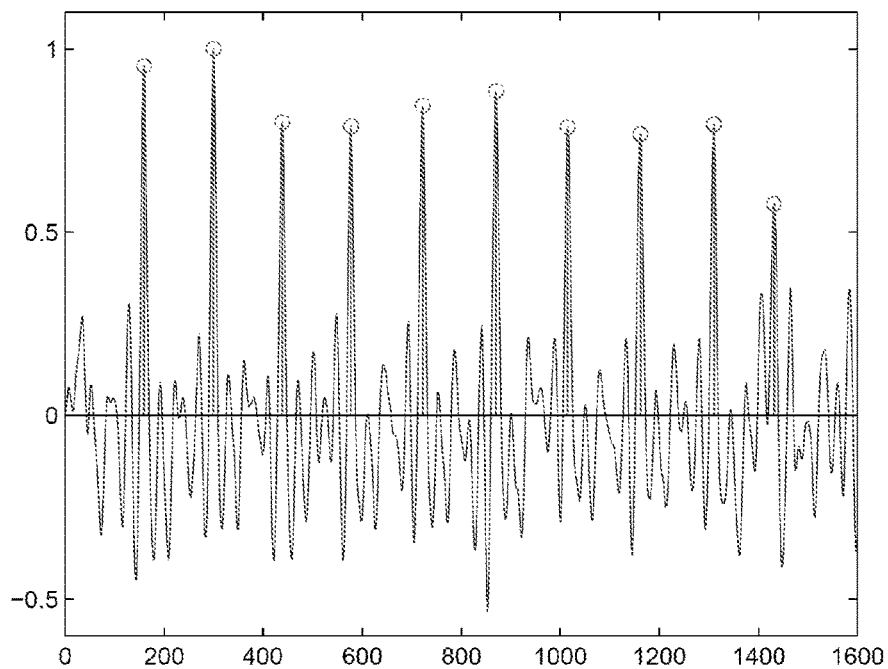
FIG. 9 illustrates an exemplary output signal corresponding to the angular ballistocardiograph signal of FIG. 7 after a specific matched filtering.

The matched filtering template may include one or more limits, for example, to maximum values, minimum values, the values of individual slopes, or to a combination of slopes. FIG. 9 illustrates an exemplary output signal corresponding to the angular ballistocardiograph signal $S_{am}$ of FIG. 7 after a specific matched filtering, which will be discussed in more detail later on.

The control unit may be configured to generate various output parameters. In the simplest form, a parameter may be indicative of radial orientation of the heart, angular velocity of the heart, or angular acceleration of the heart during the twisting motion. This output parameter may correspond to a measured, conditioned, and filtered angular ballistocardiograph signal $S_{am}$ shown in FIG. 7 or 9.

Alternatively, or additionally, a parameter may be indicative of the stroke volume of the heart of the subject. The output parameter may be generated by determining amplitude of the angular ballistocardiograph signal $S_{am}$ and using that as a value to represent the temporal stroke volume. For example, a peak amplitude, semi-amplitude, or root mean square amplitude may be used for the purpose. Since the signal is not a pure symmetric periodic wave, amplitude is advantageously measured in respect to a defined reference value, for example, from a zero point of the signal curve. Other reference values may be applied within the scope, as well.

Alternatively, or additionally, a parameter may be indicative of the heartbeat of the subject. For example, the output parameter may be generated by selecting a characteristic point of the angular ballistocardiograph signal $S_{am}$ and determining the occurrence of the characteristic point in consecutive signal sequences. A minimum or maximum value of the signal sequence may be applied as the characteristic point. The occurrence of the characteristic point may be considered as a time stamp of the heartbeat. A period between two timestamps may be considered to represent temporary beat-to-beat (B-B) time of the heart of the subject. The number of timestamps within a defined period may be applied to indicate heart rate (HR) of the subject.

Alternatively, or additionally, a parameter may be indicative of aortic opening or closing of the heart of the subject. Aortic opening (AO) and aortic closing (AC) typically show as peaks in the chest recoil effect. In measurement systems where the recoil is measured with linear acceleration means, the AO and AC peaks are quite similar in shape, but usually the AO peak is higher than the AC peak. For some subjects, the AO peak and the AC peak may, however, be almost as high, or the AC peak may even be higher than the AO peak. Also, with linear acceleration means, the posture of the subject tends to affect the shape of the signal. Due to this, measurements with linear acceleration means do not necessarily provide reliable data, especially if the subject may be allowed to be in various postures. In measurement systems where the recoil is measured by sensing angular motion with a gyroscope, the AO peak has a very distinctive shape and is therefore much more reliably distinguishable from the AC peak in the angular ballistocardiograph signal $S_{am}$.

Figure 10:
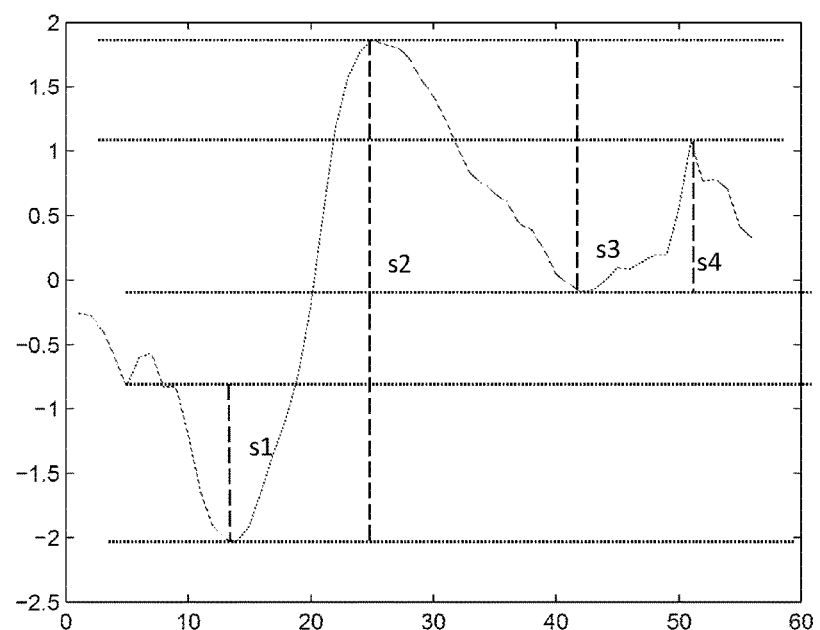
FIG. 10 illustrates a potential AO peak from the signal of FIG. 7.

Referring back to FIGS. 7 and 9, an emphasized section of the angular ballistocardiograph signal $S_{am}$ in FIG. 7 includes an AO peak that may be identified by means of matched filtering mechanism described in general earlier. FIG. 10 illustrates a potential AO peak from the signal of FIG. 5. In order to ensure that a valid AO peak is detected, surroundings of the maximum values of the angular ballistocardiograph signal $S_{am}$ may be applied in the matched filtering template. For example, the control unit may be configured to determine slopes of the signal curve, as described above, and determine a sum of a defined number of consecutive slopes. If the defined number is e.g. four, the control unit could compute a sum $S_{tot}=s1+s2+s3+s4$. A valid AO peak may be considered, for example, to exist in the range that corresponds to a maximum of sums $S_{tot}$ in the sequence.

Figure 11:
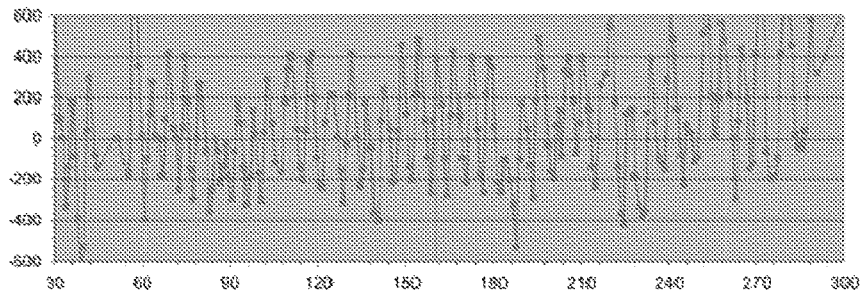
FIG. 11 illustrates exemplary values of stroke volume and heartbeat timestamps measured from a test subject.

Alternatively, or additionally, a parameter may be indicative of another vital operation that interacts with the cardiac function. Such vital operation can be, for example, respiration. FIG. 11 illustrates exemplary values of stroke volume and heartbeat timestamps in a signal measured from a test subject. It may be seen that during respiration, the stroke volume and beat-to-beat time of the heart typically change. When the lungs are empty, the stroke volume may reach its maximum values, and the beat-to-beat time may be lower. When the lungs are full, the stroke volume values are smaller and the heart beats faster. Accordingly, breathing of the subject may be seen as periodic modulation of the angular ballistocardiograph signal $S_{am}$. The frequency of the modulation may be considered to represent the breathing rate of the subject and the amplitude of the modulation may be considered to represent the depth of the breathing of the subject.

Other parameters, derivable from the angular ballistocardiograph signal $S_{am}$ and applicable for representing state of the cardiac functions of the subject may be used within the scope, as well.

Figure 12:
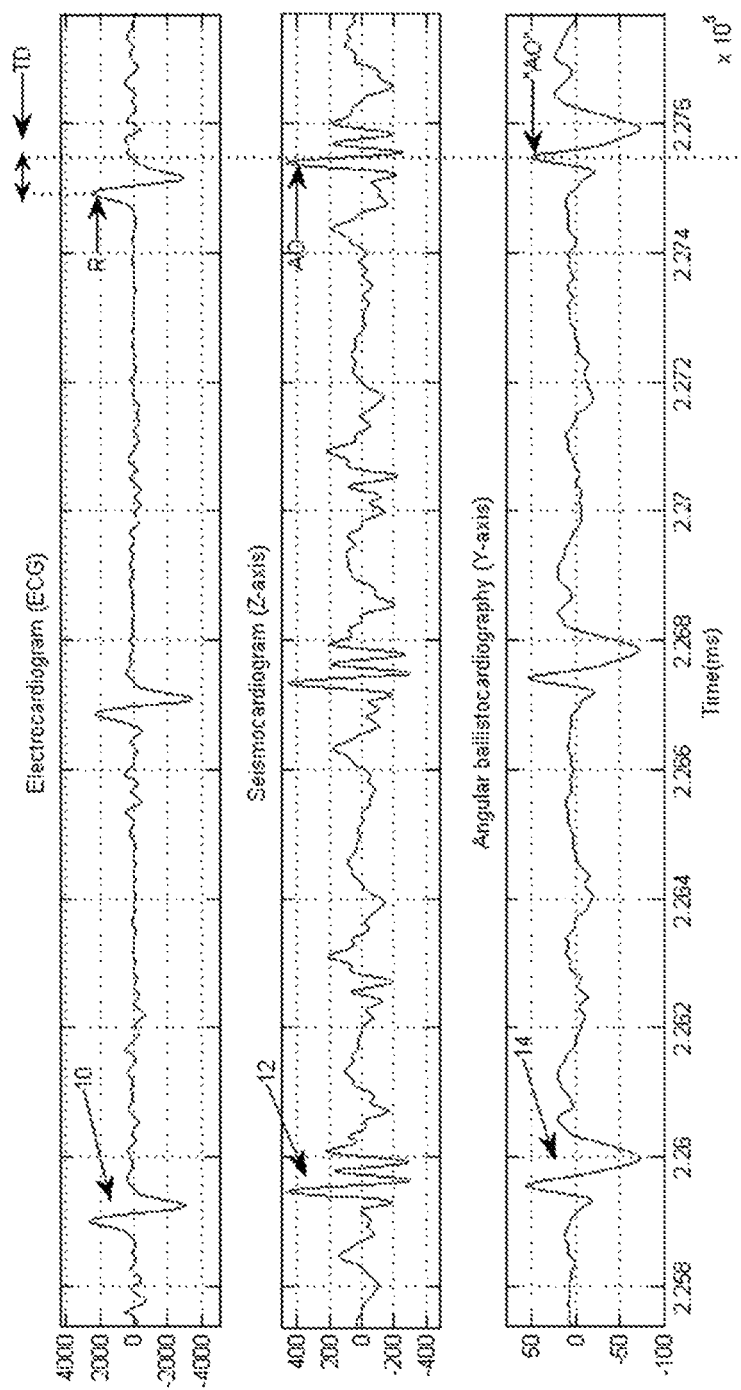
FIG. 12 illustrates measurements taken simultaneously from one test subject with various measurement technologies.

FIG. 12 illustrates measurements taken simultaneously from one test subject with the two conventional technologies and with the proposed new method. The first curve 10 shows an output signal generated with an electrocardiogram, the second curve 12 shows an output signal generated with a multi-axial accelerometer (a seismocardiogram, z-axis) and the third curve 14 shows angular ballistocardiograph signal generated with a multi-axial gyroscope (y-axis). It may be seen that the occurrences related to aortic valve opening AO (aortic rotational opening) are more distinguishable in the proposed angular ballistocardiography signal than in the multi-axial accelerometer signal.

One or more different types of output parameters may be created in the system. These parameters may be output from the system or applied in the system to indicate malfunctions and abnormalities in cardiac operation of the subject.

In an embodiment, timing of two wave patterns that repeat on the heart-beat rate of the subject may be applied to indicate abnormal cardiac operation of the subject. For example, a first signal indicative of electromagnetic phenomena related to cardiac activity may be extracted from a first wave pattern that repeats on a heart-beat rate. A second signal indicative of cardiovascular rotation may be extracted from a second wave pattern that also repeats on the heart-beat rate. The cardiovascular rotation may be measured from the rotational movement of the chest of the subject, as described above. The first signal and the second signal may be used to form timing data, each timing value of which may be indicative of a time period from a reference point of the first wave pattern belonging to one heart-beat period to a reference point of the second wave pattern belonging to the same heart-beat period. Correlation between the timing data and pacing data indicative of the heart-beat rate may be used as a parameter indicative of cardiac (mal)function and (ab)normality.

The second wave pattern may be selected such that it represents a response of the heart to the first wave pattern on the first signal. The first signal can represent, for example, an electrocardiograph ECG waveform. The first wave pattern can be, for example but not necessarily, the R-peak of the ECG waveform shown in FIG. 10, and the second wave pattern can be, for example but not necessarily, the AO peak on the angular ballistocardiography waveform shown in FIG. 12. In this case, the top of the R-peak can be used as the reference point of the first wave pattern and the top of the AO-peak can be used as the reference point of the second wave pattern, and values of timing data TD can indicate the time period from the moment of the top of the R-peak to the moment of the top of the AO-peak.

The degree of correlation between the timing data and the pacing data can be expressed, for example but not necessarily, with the aid of a correlation coefficient that can be computed according to the following equation:

$$C(j)=E\{(TD-\mu_T)\times(PD-\mu_P)\},$$

where $C(j)$ is the correlation coefficient, E is the expected value operator, i.e. E{variable} is the expected value of the variable, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods. In light of empirical results, it is advantageous that the pacing data PD has a lag of one heart-beat period with respect to the timing data TD, i.e. j=1. In this case, when the timing data TD relates to a given heart-beat period, the corresponding pacing data PD relates to the previous heart-beat period. The correlation coefficient can be expressed in a form $\sigma_{T,P}$ that it is always on the range from −1 to +1:

$$\sigma_{T,P}=C(j)/(\sigma_T\times\sigma_P),$$

where $\sigma_T$ and $\sigma_P$ are the standard deviations of the timing data and the pacing data, respectively.

FIG. 12 illustrates an exemplifying way to define the timing data TD. In this exemplifying case, the R-peak appearing on the ECG waveform and caused by depolarization of the ventricular muscle tissue represents the first wave pattern 10 repeating on the heart-beat rate, and the AO peak of the waveform indicative of cardiovascular rotation represents the second wave pattern 14 repeating on the heart-beat rate. The top of the R-peak may be applied as the reference point of the first wave pattern and the top of the AO-peak may be applied as the reference point of the second wave pattern.

It is to be noted that the given equation and the method for defining the timing data are examples only. There are numerous ways for expressing the possible correlation between the timing data and the pacing data, and the present invention is not limited to a particular way of expressing the correlation. Furthermore, it is to be noted that the correlation is not necessarily a mathematical quantity but it refers to any of a broad class of statistical relationships involving dependence, and that the correlation in its general sense does not imply or require causation.

Figure 13:
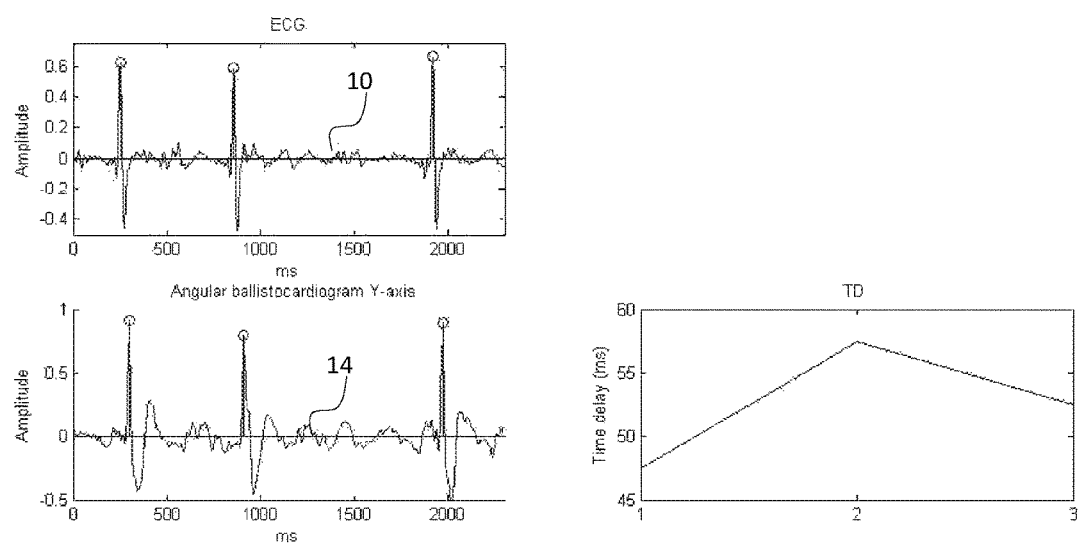
FIG. 13 illustrates generation of a parameter indicative of atrial extrasystole of the subject.

As a specific example, FIG. 13 illustrates generation of a parameter indicative of atrial extrasystole of the subject. The two graphs in the left-hand side of FIG. 13 show the first wave pattern 10 and the second wave pattern 14, as introduced in FIG. 10. The graph in the right side shows empirical values of the timing data TD obtained from these wave patterns. Each number (1,2,3) in the right-hand graph represents the time difference between the R-peak of an ECG waveform in the first wave pattern 10 and the AO-peak of a waveform indicative of cardiovascular rotation in the second wave pattern 14. As can be seen from the left-hand graphs of FIG. 13, the second beat 2 may be considered as atrial extrasystole, and the first and the third beats may be considered normal. As shown in the right-hand graph, the trend of the timing data increases during atrial extrasystole, whereas in a normal case, the trend is substantially constant or decreasing. A positive slope of in the right-hand graph in FIG. 13 illustrates a positive correlation between the timing data and the pacing data. A positive correlation between the timing data and the pacing data may thus be applied in or output from the system as a parameter indicative of atrial extrasystole of the subject.

Figure 14:
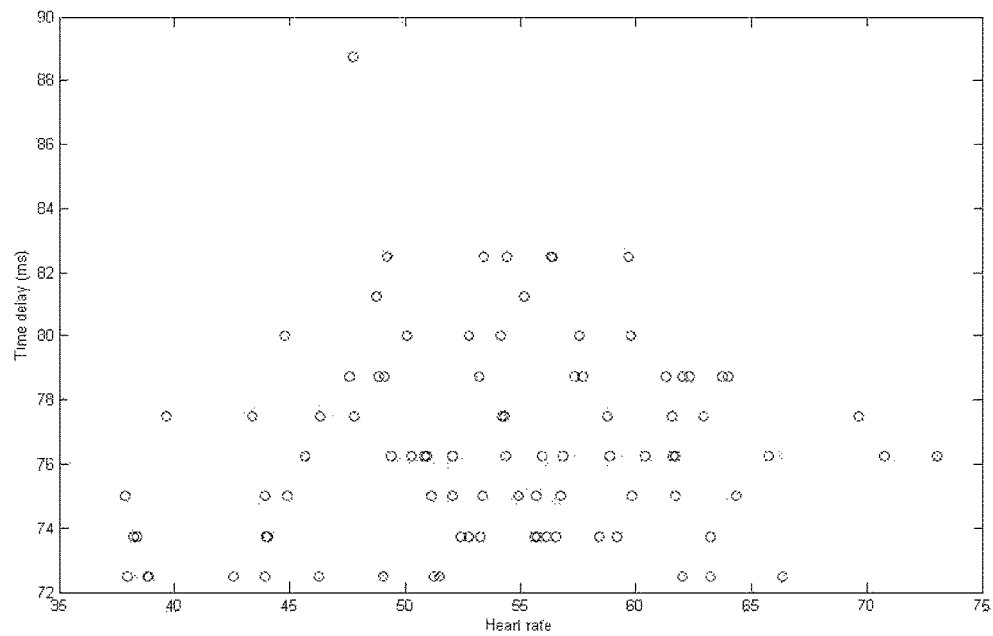
FIG. 14 shows exemplary time differences (TD) in a case of atrial fibrillation of the subject.

As another specific example, in light of empirical data, it has been noticed that, during atrial fibrillation, there is stochastic variation in the time delay (TD) between successive heart-beat periods. FIG. 14 shows time differences (TD) between the R-peak of an ECG waveform and the AO-peak of a waveform indicative of cardiovascular rotation at different heart-beat rates in an exemplifying case of atrial fibrillation of the subject.

The degree of the above-mentioned variation can be expressed with the aid of a mathematical variation-quantity that can be computed, for example, according to the following equation:

$$V = \frac{\sqrt{\frac{\sum_{i=1}^{M}(TD(i)-\mu_T)^2}{M-1}}}{\mu_T} \times 100\%,$$

where V is the variation quantity, M is the number of timing data values under consideration at the heart-beat rate under consideration, and $$\mu_T = \frac{\sum_{i=1}^{M} TD(i)}{M}.$$

In light of empirical data, the variation-quantity V can be over 10% during atrial fibrillation and about 5% in a normal case.

The system may thus be configured to produce a signal expressing atrial fibrillation in response to a situation in which the variation-quantity V is greater than a threshold. A suitable value for the threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds where each threshold represents a specific probability of atrial fibrillation or some other cardiac malfunction and/or abnormality.

In another embodiment, amplitude variation, i.e. variation of amplitude of a wave pattern repeating on the heart-beat rate on the signal may be applied to indicate abnormal cardiac operation of the subject. Amplitude variation may be detected from a signal indicative of cardiovascular rotation. The amplitude variation may be variation of amplitude of a wave pattern repeating on the heart-beat rate on the signal so that the amplitude variation includes a plurality of increases of the amplitude and a plurality of decreases of the amplitude. An indicator of cardiac malfunction and abnormality may, at least partly, be determined on the basis of the detected amplitude variation. The above-mentioned wave pattern can be, for example but not necessarily, the AO-peak of a waveform indicative of cardiovascular rotation.

Such cardiac malfunctions and abnormalities, e.g. atrial fibrillation, which may be sometimes challenging to diagnose, may however cause irregularities on the waveform of the signal indicative of cardiovascular rotation. These irregularities may be difficult to detect from waveforms of one or two heart-beat periods but they may manifest themselves in longer time periods covering several heart-beat periods so that the amplitude of the wave pattern repeating on the heart-beat rate varies more strongly than in a normal case. Therefore, the amplitude variation represents information indicative of cardiac malfunction and abnormality.

In another embodiment, time variation may be detected from the signal, where the time variation is the variation of temporal lengths of heart-beat periods. The indicator of cardiac malfunction and abnormality can be determined on the basis of both the amplitude variation and the time variation in order to improve the reliability of the information indicative of cardiac malfunctions and abnormalities.

Figure 15:
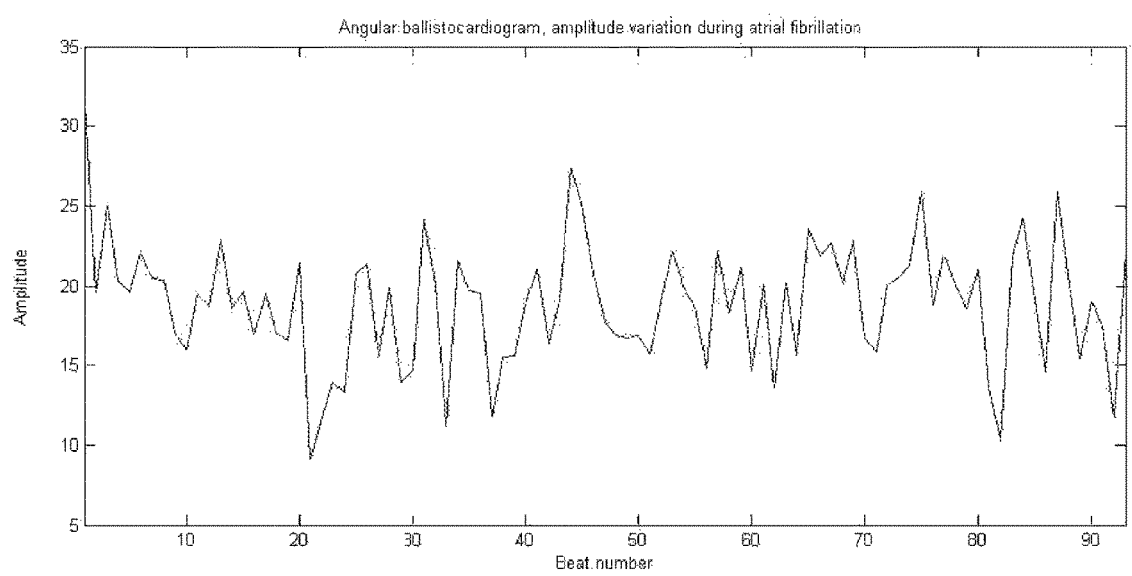
FIG. 15 illustrates amplitude variation of an exemplifying signal in a case of atrial fibrillation when a person under consideration is breathing.
Figure 16:
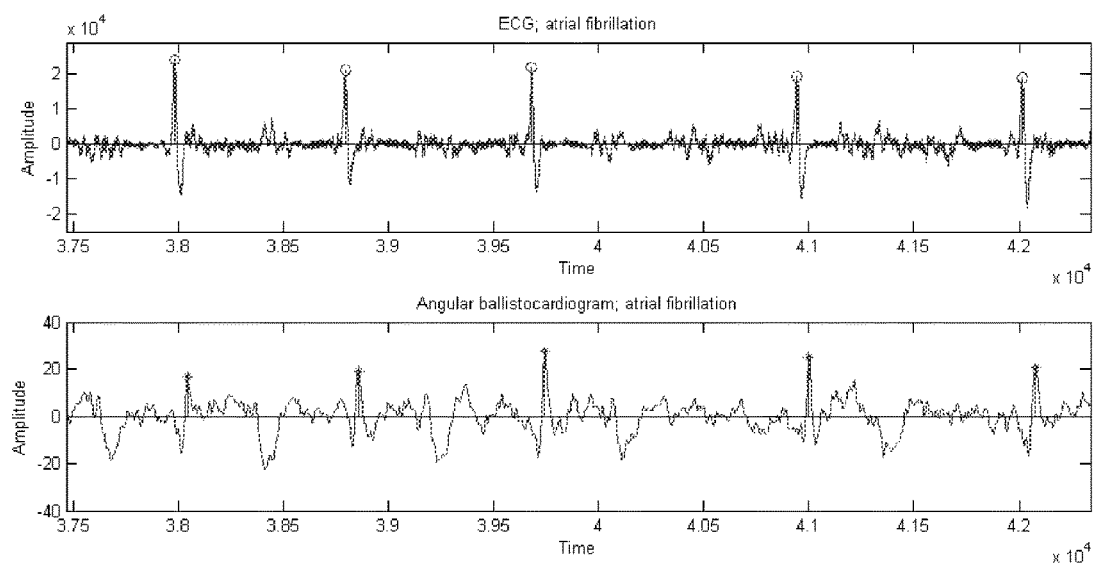
FIG. 16 illustrates an example of an ECG waveform and an angular ballistocardiogram waveform of an exemplifying signal indicative of cardiovascular rotation.

FIG. 15 illustrates amplitude variation of an exemplifying signal indicative of cardiovascular rotation over several successive heartbeats in a case of atrial fibrillation when a person under consideration is breathing. FIG. 16 illustrates an example of an ECG waveform and an angular ballistocardiogram waveform of an exemplifying signal indicative of cardiovascular rotation.

The amplitude variation quantity may be applied as a parameter indicative of cardiac operation and it can be compared to a threshold in order to detect occurrence of cardiac malfunction and abnormality. The threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds so that each threshold represents a specific probability of atrial fibrillation or some other cardiac malfunction and/or abnormality.

The amplitude variation quantity can be, for example:

$$RMS_{p-p} - AVE_{p-p},$$

where $RMS_{p-p}$ is the root-mean-square "RMS" of the detected peak-to-peak values and $AVE_{p-p}$ is the arithmetic average of the detected peak-to-peak values of the signal indicative of cardiovascular rotation. For another example, the strength of the amplitude variation can be expressed with the aid of the standard deviation of the detected peak-to-peak values, i.e. amplitude variation quantity can be the standard deviation of the detected peak-to-peak values of the signal indicative of cardiovascular rotation.

It is to be noted that there are numerous ways to express the strength of the amplitude variation and the present invention is not limited to any particular ways of expressing the strength of the amplitude variation.

For added accuracy reliability and functionality it may, however, be advantageous to use gyrocardiogram signals in combination with signals generated through other measurement technologies. For example, the angular ballistocardiograph signal can be used in combination with conventional linear ballistocardiologic (BCG) measurement data, dynamic and/or static blood pressure measurement, Photoplethysmography (PPG), ultrasonic or magnetic measurement equipment or ECG monitors. Combination of the signals may be done in the control unit of the local node or in a remote node of FIG. 6.

For early and efficient detection of anomalies in the cardiac operation, angular ballistocardiograph signals of a subject or parameter values generated from the angular ballistocardiograph signals of the subject may be stored in a local or remote database. The system may then be configured to automatically compare fresh data to a selected piece of stored information, and create an alarm if the deviation of new values from the stored information exceeds a predefined threshold.

It is apparent to a person skilled in the art that as technology advances, the basic idea of the invention can be implemented in various ways. The invention and its embodiments are therefore not restricted to the above examples, but they may vary within the scope of the claims

The invention claimed is:

1. A system, comprising:
 a gyroscope configured to obtain, on a chest of a subject and using Coriolis effect, an angular ballistocardiograph signal indicative of rotational recoil movement on the chest of the subject in response to cardiovascular rotation within the chest of the subject; and
 a signal processor configured to generate from the angular ballistocardiograph signal, measured values of an output parameter indicative of at least one of a radial orientation of a heart of the subject, an angular velocity of the heart, or an angular acceleration of the heart during cardiac operation of the subject.

2. The system of claim 1, further comprising:
 a sensor unit comprising the gyroscope; and
 a control unit coupled to the sensor unit, to receive the angular ballistocardiograph signal.

3. The system of claim 2, wherein the sensor unit is configured to be attached to an exterior of the chest of the subject, and
 wherein the control unit is communicatively coupled to the sensor unit to receive the angular ballistocardiograph signal.

4. The system of claim 2, wherein the system comprises a mobile computing device.

5. The system of claim 2, wherein the system includes a remote node, communicatively coupled to the control unit.

6. The system of claim 2, wherein the control unit is configured to store angular ballistocardiograph signals of the subject or measured values generated from the angular ballistocardiograph signals of the subject into a local or remote database.

7. The system of claim 6, wherein the control unit is configured to compare new measured values to a selected piece of stored information in the local or remote database, and create an alarm if a deviation of new values from the stored information exceeds a predefined threshold.

8. The system of claim 1, wherein the gyroscope is configured to sense rotational movement in a sense direction that is parallel to an axis of rotation, and
wherein the sense direction of the sensor unit is configured to be aligned to a symmetry plane of a body of the subject.

9. The system of claim 8, wherein the subject is a human and the symmetry plane is a sagittal plane of the human subject.

10. The system of claim 1, wherein the signal processor is configured to generate from the angular ballistocardiograph signal a measured value representing temporary stroke volume of the heart of the subject.

11. The system of claim 10, wherein the angular ballistocardiograph signal is sequential,
wherein the signal processor is configured to determine an amplitude of a sequence of the angular ballistocardiograph signal, and
wherein the signal processor is configured to use the amplitude to generate a measured value representing temporary stroke volume during the sequence of the angular ballistocardiograph signal.

12. The system of claim 1, wherein the signal processor is configured to generate from the angular ballistocardiograph signal a measured value representing beat-to-beat time or heart rate of a heart of the subject.

13. The system of claim 1, wherein the signal processor is configured to generate from the angular ballistocardiograph signal a measured value representing aortic closing or aortic opening of a heart of the subject.

14. The system of claim 1, wherein the signal processor is configured to generate from the angular ballistocardiograph signal a measured value representing another vital operation of the subject.

15. The system of claim 14, wherein the vital operation is respiration.

16. The system of claim 1, wherein the signal processor is configured to:
determine amplitude variation of the angular ballistocardiograph signal; and
generate measured values of the output parameter from the determined amplitude variation of the angular ballistocardiograph signal.

17. The system of claim 16, wherein the signal processor is configured to determine the amplitude variation from wave patterns repeating on a heart-beat rate on the angular ballistocardiograph signal so that the amplitude variation includes two or more increases of the amplitude and two or more decreases of the amplitude.

18. The system of claim 17, wherein the signal processor is configured to determine the amplitude variation from aortic opening (AO) wave patterns repeating on the heart-beat rate on the angular ballistocardiograph signal.

19. The system of claim 16, wherein the signal processor is configured to use the output parameter to indicate abnormal cardiac operation of the subject.

20. The system of claim 19, wherein the abnormal cardiac operation results from atrial extrasystole or atrial fibrillation.

21. The system of claim 1, wherein the signal processor is configured to:
extract from a signal indicative of electromagnetic phenomena related to cardiac activity a first wave pattern repeating on a heart-beat rate;
extract from the angular ballistocardiograph signal a second wave pattern repeating on the heart-beat rate;
form timing data, a value of the timing data being indicative of a time period from a reference point of the first wave pattern belonging to one heart-beat period to another reference point of the second wave pattern belonging to the same heart-beat period; and
use the timing data to generate measured values of the output parameter.

22. The system of claim 21, wherein the signal processor is configured to:
determine a correlation between pacing data indicative of the heart-beat rate and the timing data; and
use the correlation to generate measured values of the output parameter.

23. The system of claim 21, wherein the signal processor is configured to:
determine stochastic variation in the timing value between successive heart-beat periods; and
use the stochastic variation to generate measured values of the output parameter.

24. The system of claim 1, wherein the sensor unit is configured to be positioned on a pectoral part of an upper torso of the subject.

25. The system of claim 1, wherein the sensor unit is configured to be positioned on a backside part of an upper torso of the subject.

26. The system of claim 1, wherein the sensor unit is configured to obtain the angular ballistocardiograph signal with a microelectromechanical gyroscope.

27. A method, comprising:
obtaining with a gyroscope on a chest of a subject, and using Coriolis effect, an angular ballistocardiograph signal indicative of rotational recoil movement of the chest of the subject in response to cardiovascular rotation within the chest; and
generating from the angular ballistocardiograph signal measured values of an output parameter indicative of at least one of a radial orientation of a heart of the subject, an angular velocity of the heart, or an angular acceleration of the heart during cardiac operation of the subject.

28. The method of claim 27, including:
attaching a sensor unit comprising the gyroscope to an exterior of the chest of the subject; and
forwarding the angular ballistocardiograph signal to a control unit communicatively coupled to the sensor unit.

29. The method of claim 28, including forwarding the measured values to a remote node, the remote node being communicatively coupled to the control unit.

30. The method of claim 28, further comprising positioning the sensor unit on a pectoral part of an upper torso of the subject.

31. The method of claim 28, further comprising positioning the sensor unit on a backside part of an upper torso of the subject.

32. The method of claim 28, further comprising obtaining the angular ballistocardiograph signal with a microelectromechanical gyroscope.

33. The method of claim 27, including:
sensing rotational movement in a sense direction that is parallel to an axis of rotation; and
aligning the sense direction to a symmetry plane of a body of the subject.

34. The method of claim 33, wherein the subject is a human and the symmetry plane is a sagittal plane of the human subject.

35. The method of claim 27, further comprising generating, from the angular ballistocardiograph signal, a measured value representing temporary stroke volume of a heart of the subject.

36. The method of claim 27, further comprising generating, from the angular ballistocardiograph signal, a measured value representing beat-to-beat time or heart rate of a heart of the subject.

37. The method of claim 27, further comprising generating, from the angular ballistocardiograph signal, a measured value representing aortic closing or aortic opening of a heart of the subject.

38. The method of claim 27, further comprising generating, from the angular ballistocardiograph signal, a measured value representing another vital operation of the subject.

39. The method of claim 38, wherein the vital operation is respiration.

40. The method of claim 27, further comprising storing angular ballistocardiograph signals of the subject or measured values generated from the angular ballistocardiograph signals of the subject in a local or remote database.

41. The method of claim 40, further comprising:
comparing new measured values to a selected piece of stored information in the local or remote database; and
creating an alarm if the deviation of new values from the stored information exceeds a predefined threshold.

42. The method of claim 27, further comprising
determining amplitude variation of the angular ballistocardiograph signal;
generating measured values of the output parameter from the amplitude variation of the angular ballistocardiograph signal.

43. The method of claim 42, further comprising determining the amplitude variation from wave patterns repeating on the heart-beat rate on the angular ballistocardiograph signal so that the amplitude variation includes two or more increases of the amplitude and two or more decreases of the amplitude.

44. The method of claim 43, further comprising determining the amplitude variation from aortic opening (AO) wave patterns repeating on the heart-beat rate on the angular ballistocardiograph signal.

45. The method of claim 27, further comprising:
extracting from a signal indicative of electromagnetic phenomena related to cardiac activity a first wave pattern repeating on a heart-beat rate;
extracting from the angular ballistocardiograph signal a second wave pattern repeating on the heart-beat rate;
forming timing data, a timing value of the timing data being indicative of a time period from a reference point of the first wave pattern belonging to one heart-beat period to another reference point of the second wave pattern belonging to the same heart-beat period; and
using the timing data to generate measured values of the output parameter.

46. The method of claim 45, wherein the angular ballistocardiograph signal is sequential, and the method further comprises:
determining an amplitude of a sequence of the angular ballistocardiograph signal; and
using the amplitude to generate a measured value representing temporary stroke volume during the sequence of the angular ballistocardiograph signal.

47. The method of claim 45, further comprising:
determining a correlation between the timing data and pacing data indicative of a heart-beat rate;
using the correlation to generate measured values of an output parameter.

48. The method of claim 47, further comprising
determining stochastic variation in the timing value between successive heart-beat periods; and
using the stochastic variation to generate measured values of the output parameter.

49. The method of claim 42, further comprising using the output parameter to indicate abnormal cardiac operation of the subject.

50. The method of claim 49, wherein the abnormal cardiac operation results from atrial extrasystole or atrial fibrillation.

51. A computer program product embodied on a non-transitory computer-readable medium, said computer-readable medium encoding instructions for executing the method of claim 27 in a cardiac monitoring system when run on a computer.

52. A system, comprising:
gyroscope means for obtaining on a chest of a subject, and using Coriolis effect, an angular ballistocardiograph signal indicative of rotational recoil movement on the chest of the subject in response to cardiovascular rotation within the chest of the subject; and
signal processing means for generating, from the angular ballistocardiograph signal, measured values of an output parameter indicative of at least one of a radial orientation of a heart of the subject, an angular velocity of the heart, or an angular acceleration of the heart during cardiac operation of the subject.

* * * * *